(12) United States Patent
Chamanzar et al.

(10) Patent No.: US 12,661,054 B2
(45) Date of Patent: Jun. 23, 2026

(54) SYSTEM AND METHOD FOR DEEP LEARNING FOR TRACKING CORTICAL SPREADING DEPRESSION USING EEG

(71) Applicant: CARNEGIE MELLON UNIVERSITY, Pittsburgh, PA (US)

(72) Inventors: Alireza Chamanzar, Pittsburgh, PA (US); Xujin Liu, Pittsburgh, PA (US); Lavender Y. Jiang, Pittsburgh, PA (US); Kimon A. Vogt, Pittsburgh, PA (US); José M.F. Moura, Pittsburgh, PA (US); Pulkit Grover, Pittsburgh, PA (US)

(73) Assignee: CARNEGIE MELLON UNIVERSITY, Pittsburgh, PA (US)

( * ) Notice: Subject to any disclaimer, the term of this patent is extended or adjusted under 35 U.S.C. 154(b) by 178 days.

(21) Appl. No.: 18/011,351

(22) PCT Filed: Apr. 27, 2022

(86) PCT No.: PCT/US2022/026524
§ 371 (c)(1),
(2) Date: Dec. 19, 2022

(87) PCT Pub. No.: WO2022/235467
PCT Pub. Date: Nov. 10, 2022

(65) Prior Publication Data
US 2024/0050020 A1 Feb. 15, 2024

Related U.S. Application Data

(60) Provisional application No. 63/183,156, filed on May 3, 2021.

(51) Int. Cl.
*A61B 5/372* (2021.01)
*A61B 5/00* (2006.01)

(52) U.S. Cl.
CPC ............ *A61B 5/372* (2021.01); *A61B 5/7267* (2013.01)

(58) Field of Classification Search
CPC ......... A61B 5/097; A61B 5/082; A61B 5/087; A61B 2560/0406; A61B 5/372;
(Continued)

(56) References Cited

U.S. PATENT DOCUMENTS

2009/0258844 A1    10/2009    Hochman
2015/0134580 A1*   5/2015     Wilson ................... G06N 3/043
                                                      706/25
(Continued)

FOREIGN PATENT DOCUMENTS

CN        110876626  A  *  3/2020   ............. G06N 20/10
CN        107992842  B  *  8/2020   ........... G06V 40/168
(Continued)

OTHER PUBLICATIONS

Ramyead et al, "Prediction of psychosis using neural oscillations and machine learning in neuroleptic-naive at-risk patients", Oct. 2015, The World Journal of Biological Psychiatry, 1-11 (Year: 2015).*
(Continued)

*Primary Examiner* — Alex M Valvis
*Assistant Examiner* — Shawn Curtis Broughton
(74) *Attorney, Agent, or Firm* — KDW FIRM PLLC

(57) ABSTRACT

Disclosed herein is a system and method implementing an automated, generalizable model for tracking cortical spreading depressions using EEG. The model comprises convolutional neural networks and graph neural networks to leverage both the spatial and the temporal properties of CSDs in the detection. The trained model is generalizable to different head models such that it can be applied to new patients without re-training. Further, the model is scalable to differ-
(Continued)

ent densities of EEG electrodes, even when trained on a specific electrode density.

13 Claims, 1 Drawing Sheet

(58) Field of Classification Search
CPC ................ A61B 5/7267; A61B 5/7264; G01N 33/0031; G01N 33/497; G01N 33/56983; G01N 2800/00
See application file for complete search history.

(56) References Cited

U.S. PATENT DOCUMENTS

| | | | |
|---|---|---|---|
| 2017/0215759 A1 | 8/2017 | Dudek et al. | |
| 2019/0038167 A1* | 2/2019 | Jones ..................... | A61B 5/316 |
| 2019/0180878 A1 | 6/2019 | Fridriksson et al. | |
| 2020/0359925 A1* | 11/2020 | Boutelle ................ | A61B 5/316 |
| 2021/0196964 A1* | 7/2021 | Schnell .............. | A61N 1/37247 |
| 2022/0008728 A1* | 1/2022 | Phillips .............. | A61N 1/36175 |
| 2022/0032074 A1* | 2/2022 | Akbari ............... | A61B 5/14553 |
| 2023/0075205 A1* | 3/2023 | Moran ............... | A61N 1/37211 |

FOREIGN PATENT DOCUMENTS

| | | | | | |
|---|---|---|---|---|---|
| CN | 113576491 A | * | 11/2021 | ............. | A61B 5/369 |
| WO | WO-2021046273 A1 | * | 3/2021 | ............. | G16H 50/20 |

OTHER PUBLICATIONS

Sun et al, "A novel end-to-end 1D-ResCNN model to remove artifact from EEG signals", Apr. 23, 2020, Neurocomputing 404, 108-121 (Year: 2020).*

Li et al, "Classify EEG and Reveal Latent Graph Structure with Spatio-Temporal Graph Convolutional Neural Network", 2019, IEEE International Conference on Data Mining (ICDM), 389-398 (Year: 2019).*

Chamanzar et al., "An Algorithm for Automated, Noninvasive Detection of Cortical Spreading Depolarizations Based on EEG Simulations" IEEE Transactions on Biomedical Engineering, vol. 66, No. 4, Apr. 2019.

International Search Report and Written Opinion for Application No. PCT/US22/26524, mailed Aug. 18, 2022, 12 pages.

Wang, Yujiang et al. "Computational modeling of neurostimulation in brain diseases." Progress in brain research vol. 222 (2015): 191-228.

Chamanzar et al., "Automated, Scalable and Generalizable Deep Learning for Tracking Cortical Spreading Depression Using EEG," 2021 10th International IEEE/EMBS Conference on Neural Engineering (NER), 2021, pp. 416-441.

* cited by examiner

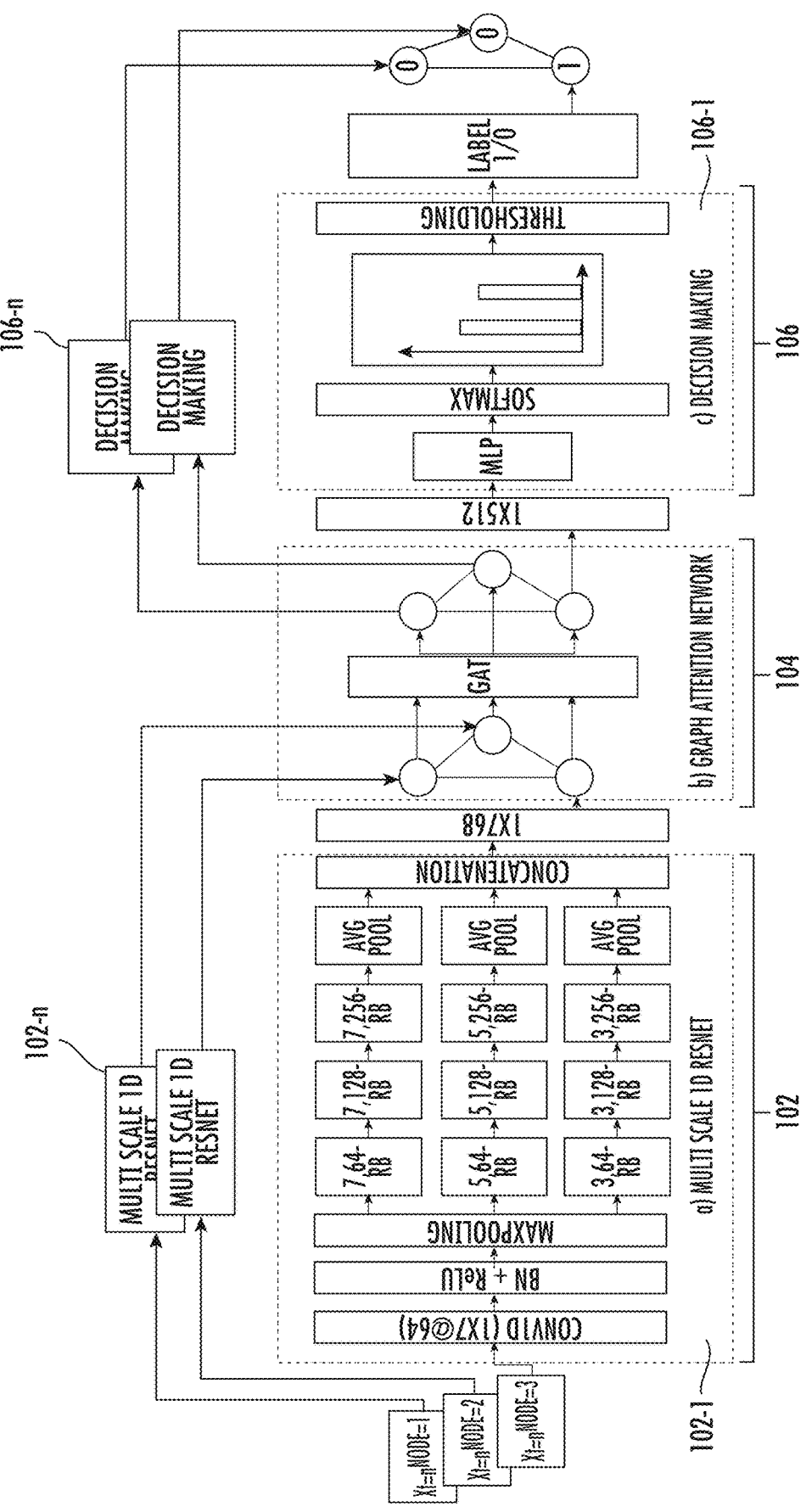

SYSTEM AND METHOD FOR DEEP LEARNING FOR TRACKING CORTICAL SPREADING DEPRESSION USING EEG

RELATED APPLICATIONS

This application is a national phase filing under 35 U.S.C. § 371 claiming the benefit of and priority to International Patent Application No. PCT/US22/26524, filed Apr. 27, 2022, entitled "SYSTEM AND METHOD FOR DEEP LEARNING FOR TRACKING CORTICAL SPREADING DEPRESSING USING EEG", which claims the benefit of U.S. Provisional Patent Application No. 63/183,156, filed May 3, 2021. The contents of these applications are incorporated herein in their entireties.

BACKGROUND OF THE INVENTION

Cortical Spreading Depressions (CSDs) are waves of depression in spontaneous neural activity that arise due to neurochemical changes in the brain. CSDs propagate relatively slowly across the cortical surface, at a rate of approximately 1-8 mm/min. Increasing evidence suggests that CSDs can cause secondary brain injuries after traumatic brain injuries (TBIs), stroke, and hemorrhages. Early detection and continuous monitoring of CSD propagation is critical to reduce permanent damage to the brain tissue in patients with brain injuries.

The ability to detect CSDs reliably and to infer how the wave is traveling would be a major factor affecting clinical decision-making. Therefore it would be desirable to provide the ability to detect when there is a CSD episode (i.e., a wave of CSD in the brain), and to track its propagation in the sensor (e.g., an EEG electrode) space to inform which electrodes are most affected during each time interval in a series of time intervals. The latter provides the clinician with a sense of the location of the wave.

SUMMARY OF THE INVENTION

Disclosed herein is a non-invasive deep learning approach for tracking cortical spreading depressions (CSDs) in scalp electroencephalography (EEG) signals. The method, which is referred to herein as a CSD spatially aware convolutional network or CSD-SpArC, combines a convolutional neural network, which extracts temporal features from the EEG signal of each EEG electrode, with a graph neural network, which exploits the spatial structure of EEG signals on the scalp.

Using EEG, this combination of networks is able to detect even the narrowest CSDs (informed by widths observed in the real world), with less than a 1.3% "post-stitching" false alarm rate. The network is further used to track CSD wave propagation by detecting when the recording at each electrode is affected substantially by the propagating wave, quantifying its spatio-temporal tracking accuracy. The network is scalable to different densities of EEG electrodes and is generalizable to different head models.

The objective of the invention is to detect when the CSD occurs and to track which EEG electrodes are most affected by CSDs as they propagate.

BRIEF DESCRIPTION OF THE DRAWINGS

FIG. 1 is a block diagram of one exemplary architecture of a model for detecting CSD.

DETAILED DESCRIPTION

Disclosed herein is an automated, generalizable model for tracking CSDs using EEG. Two notions of generalizability are defined. First, generalizability to different patients (head models), which means that the trained model can be applied to new patients with little or no retraining of the model. Second, scalability to different densities of electrodes, which means that the model, when trained on a specific electrode density, can be applied, with little or no retraining, to other electrode densities to track CSDs.

The model combines convolutional neural networks (CNNs) and graph neural networks (GNNs). The CNNs have local connections and shared weights that extract localized multi-scale features and construct highly-expressive representations based on regular grids of data (e.g., images, texts, and time series). The GNNs are a generalization of CNNs to irregular grids (i.e., graph structures such as 3D meshes). EEG recordings are temporal on a regular grid (i.e., a 1D time series at each electrode), where a CNN is used to extract temporal features for each electrode, and spatial on an irregular grid (i.e., a 3D electrode mesh), where a GNN is utilized to extract spatial information.

The spatio-temporal nature of the information of CSD waves in EEG signals using a deep learning framework is exploited by the invention. The deep learning framework comprises: (1) a CNN to extract temporal features from the preprocessed signals of each electrode; (2) a GNN to aggregate the temporal features and to exploit the spatial structure of electrode locations on the scalp to extract spatial information; and (3) a classifier, for example, a multilayer perceptron (MLP), to classify the presence or absence of CSD wavefronts at each electrode location in small non-overlapping time intervals.

The scalability of the disclosed invention, which is referred to herein as CSD-SpArC (CSD spatially aware convolutional network), has been proven using simulations on a wide range of EEG electrode densities, from a low-density grid of 20-electrode standard EEG caps, to higher densities with up to 256 electrodes at 10-5 standard locations. This makes it possible to exploit the large amount of low-density EEG data from continuous recordings at intensive care units to train the CSD-SpArC for higher densities of EEGs, for which there is not much CSD data available. Additionally, the generalizability has been proven with respect to a plurality of different head models. This provides a system that can provide rapid detection of CSDs for patients as they arrive at hospitals.

The dataset generation process, the data labeling at each electrode, the EEG preprocessing steps and details of the CSD-SpArC model will now be explained.

Dataset Generation

EEG signals of CSD waves can be simulated using the following process: First, 3D head models of 4 healthy individuals are preprocessed and extracted from an open-source magnetic resonance imaging (MRI) dataset. Second, homogeneous annulus shaped CSD waves are simulated on a real brain model, with the origin chosen randomly on the conical surface, while excluding the bottom of the brain where there is no EEG electrode coverage. Next, spontaneous brain activity is generated using some simplifying assumptions, using a normal random process, and brain activity is suppressed at the locations and time points where CSD wavefronts are to be located. The amplitude of the suppressed signal at the simulated CSD wave is ~25% of the simulated normal brain signals. This amplitude reduction is chosen based on the average of the reported range of CSD depressions. Lastly, leadfield matrices (A) based on the extracted head models are estimated and applied to the simulated brain signals to obtain scalp EEG signals (i.e., readings).

Binary Labeling of Data at Each Electrode Across Time for Training

The model is trained using binary labels that denote whether the signal of an electrode at a specific time point is substantially affected by CSD waves. To extract these binary labels, the brain sources corresponding to the 30% largest elements in the $i^{th}$ row of the leadfield matrix A are examined, and, if at least one of these sources at time t indicates a CSD depression, the label 'T' is assigned to the signal of the $i^{th}$ electrode at time t.

CSD Spatially Aware Convolutional Network (CSD-SpArC)

EEG Preprocessing—Preprocesing of the simulated EEG signals is performed to improve the signal-to-noise-ratio (SNR) of CSD depressions in the simulated EEG signals. The preprocessing techniques include Laplacian spatial filtering (for high density EEG caps with 128 and 256 electrodes), average power calculation, envelope extraction (e.g., using a sliding time window of 40 s), and cross-correlation (e.g., with 2-minute negative pulse) for each signal. In addition, the distribution of training, validation, and test datasets are normalized separately by mean subtraction and standard deviation division. The preprocessed signal is then downsampled (e.g., with a temporal step size of 6 s) before being fed into the network. This downsampling reduces the computational complexity of the network, while maintaining the required temporal information of the preprocessed signal to track CSD waves. The preprocessed signal, after the envelope extraction and cross-correlation, is concentrated in a very low frequency band. In some cases, the temporal width of depression is on the order of minutes.

Training Algorithm—A deep learning framework is used, which includes, in some embodiments, a CNN architecture called Multi Scale 1D ResNet, a GNN architecture called a graph attention network and a multilayer perceptron classifier.

One embodiment of the model of the invention is shown in block diagram form in FIG. 1. The first part of the network comprises multiple CNNs 102-1 . . . 102-n each of which performs temporal feature extraction on preprocessed scalp EEG signals from a single EEG electrode. Each CNN 102 consists of a 1D convolution layer, an activation function which may be, for example, a ReLU function, a pooling layer and multiple residual blocks. In some embodiments, each CNN 102 may comprise a Multi-Scale 1D ResNet. The 1D convolutional filters may be of various sizes and residual connections, which are known to improve time series classification. In FIG. 1, "m, n-RB" denotes a residual block of n filters, each of length m.

CSD detection at time t is performed, in one embodiment, for non-overlapping 5-min windows of the preprocessed signals from EEG electrodes, where t is the midpoint of the window. The binary labels of the midpoints are used as the CSD ground truth for the corresponding time windows. The 5-min windows from all electrodes are fed as a batch into the ResNet to extract temporal features for each electrode.

The extracted temporal features are aggregated and input to graph attention network (GAT) 104 to exploit the spatial information in the aggregated signals. The GAT model 104 is constructed using learnable attention layers to aggregate the incoming feature vectors to a node, where the attention score calculations are based on a k-nearest neighbor (k-NN) graph. In one embodiment, the GAT comprises 6 attention heads, residual connections, 2-4 layers, 500-600 hidden units, and a LeakyReLU activation function. The k-NN graph is a geometric graph that thresholds a distance, for example, the Euclidian distance, between each pair of EEG electrodes on the scalp.

The classifiers 106-1 . . . 106-n for each node/electrode, in one embodiment, use a MLP, followed by a Softmax layer to generate the spatio-temporal probability map of CSD. For example, a threshold of 0.75 is used to extract the binary outputs (1 for "CSD" and 0 for "no CSD") from the probability distribution of CSD produced by the network.

Finally, recognizing that CSDs only substantially affect a few electrodes during each time interval, the binary values at each electrode are stitched together, using, in one embodiment, a sliding time window of 10 min, with the assumption that each CSD spreads for at least 10 min. If there are at least 2 non-zero values in the time window, then a "temporal binary label" of 1 is assigned to the 10-min window. The consecutive "1's" in the union of these temporal labels, across all electrodes, is declared as a single CSD episode.

Training Process—In one instance, CSD-SpArC was trained on 5,850 simulated CSD episodes with varying length in the range of of 30-205 minutes, different speeds of propagation, in the range of 0-8 mm/min (with step size of 0.5 mm/min), and different widths of wavefronts in the range of 0.5-6.5 cm, (with step size of 0.5 cm), based on three different head models. The dataset included 10 simulated episodes for each combination of width, speed, and head model. For each of the different densities of EEG electrodes (20, 32, 64, 128, and 256 at 10-5 standard locations), a model is trained. To prevent overfitting, dropouts are used on all layers, except CNN, with P=0.5. The optimal combination of hyperparameters is found through validation using an open-source hyperpararameter optimization framework. The hyperparameters in CSD-SpArC are optimized over the following ranges: learning rate in ($10^{-5}$, $10^{-3}$), k in k-NN graph for GAT in ($\lceil N/10 \rceil$, $\lceil N/2 \rceil$) where N is the number of EEG electrodes, weight decay in ($5×10^{-4}$, $10^{-2}$), hidden layers of GAT in (2,4), and hidden units in (400,700).

Implementation Details: CSD simulations and preprocessing may be implemented in Matlab. The model may be trained and tested in PyTorch, using a batch size of 40 windows with total training iterations of 10 epochs with early stopping on validation loss of patience of 2 epochs.

Detection Performance Metrics: The spatio-temporal tracking accuracy, defined for detecting CSDs at non-overlapping time intervals, is the degree of agreement between the binary ground truth labels of CSD and the binary outputs of the model, measured using Cohen's kappa statistic (k). The standard error of k(SE(k)) is also provided. The average false positive rate, $$FPR = \frac{FP}{FP + TN'}$$

where FP is the number of false positives and TN is the number of true negatives) is reported. FPR is also reported based on the temporal binary labels (see the stitching process described above), which is referred to as "post-stitching" FPR herein.

Proof of Concept

The performance of CSD-SpArC for generalizability, scalability, and a range of CSD widths was experimentally verified.

Performance on Varying Ranges of CSD Width—The width of CSD wavefronts varies in different neurological diseases and scenarios (e.g., 0.8 to 6.4 cm in TBI). The performance of CSD-SpArC was tested on different widths of CSD wavefronts using different densities of EEG electrodes. The trained model is tested on a simulated dataset with 4 different ranges of CSD widths (0.5-2, 2-3.5, 3.5-5 and 5-6.5 (cm) with 0.5 cm step size) and a speed range of 2 to 8 mm/min (with step size of 2 mm/min) for each width range, across three different head models and for five different EEG densities (20 to 256 electrodes). Table 1 below summarizes the results of CSD detection for different widths of wavefronts and different EEG densities. As expected, the tracking accuracy increases as the number of EEG electrodes increases and as the CSD waves become wider, with the best accuracy of 86.65%±0.60 for detecting the widest CSD waves (5-6.5 cm) using the highest density EEG (256 electrodes).

TABLE 1

| k ± SE(k) | | Trained On | | | | |
| --- | --- | --- | --- | --- | --- | --- |
| | | 20 | 32 | 64 | 128 | 256 |
| CSD | 0.5-2 | 34.50% ± 21.87 | 40.52% ± 14.75 | 42.85% ± 10.23 | 47.71% ± 6.88 | 57.46% ± 4.10 |
| Width | 2-3.5 | 67.24% ± 6.35 | 72.56% ± 4.34 | 72.65% ± 3.07 | 72.73% ± 2.26 | 75.62% ± 1.46 |
| (cm) | 3.5-5 | 81.26% ± 3.00 | 82.40% ± 2.33 | 83.22% ± 1.63 | 83.25% ± 1.18 | 83.98% ± 0.81 |
| | 5-6.5 | 84.00% ± 2.26 | 85.94% ± 1.73 | 85.37% ± 1.25 | 85.86% ± 0.88 | 86.65% ± 0.60 |

Although non-invasive detection of CSD is challenging, the narrowest CSD waves (0.5-2 cm) can still be detected using CSD-SpArC using the highest density EEG (256 electrodes) with a tracking accuracy of 57.46%±4.10 and an average FPR of less than 1.43%. CSD-SpArC also detects CSD waves as narrow as 2 cm using only 20 EEG electrodes with a tracking accuracy of 67.24%±6.35 and an average FPR of less than 6.4%. Additionally, high-density EEG (256 electrodes) detect all CSD episodes, even the narrowest ones, with less than 1.3% "post-stitching" FPR.

Generalizability—To test the generalizability of CSD-SpArC to new head models (unseen by the network) the model was trained on three head models, on a simulated CSD dataset with different widths of wavefronts (0.5, 2, 5, and 6 cm) and two different speeds of propagation (2 and 4 mm/min). CSD-SpArC, trained in this manner, successfully detects and tracks CSD waves in the head model with greater than 75% tracking accuracy and less than 3% FPR using 20 or more electrodes. CSD-SpArC generalizes without any retraining and/or fine-tuning the parameters in the model.

Scalability—The model easily adapts to different densities and placements of EEG electrodes. This makes CSD-SpArC scalable to higher or lower densities of EEG electrodes. The scalability performance of CSD-SpArC was tested as follows: The trained model is used on a specific density of EEG electrodes (e.g., 20-electrodes), and was tested on a simulated test dataset of other densities (e.g., 32, 64, 128, and 256 electrodes). Each test set includes CSD episodes with different widths (0.5, 2, 4, and 6 cm) and speeds (1, 3, 5, 7 mm/min), for three different head models. Table 2 shows the results of scalability tests, with the training EEG densities across columns, and test densities across rows. The results confirm the scalability of CSD-SpArC for any combination of train-test electrode densities with an accuracy of 76.7%±1.1 and a FPR of less than 2.1% for a model which is trained on a low-density EEG (with only 20 electrodes) and tested on a high-density EEG (with 256 electrodes).

fall within the scope of the invention are possible. Specifically, many variations of the architecture of the model could be used to obtain similar results. The invention is not meant to be limited to the particular exemplary model disclosed herein. Moreover, it is to be understood that the features of the various embodiments described herein were not mutually exclusive and can exist in various combinations and permutations, even if such combinations or permutations were not made express herein, without departing from the spirit and scope of the invention. Accordingly, the method and apparatus disclosed herein are not to be taken as limitations on the invention but as an illustration thereof. The scope of the invention is defined by the claims which follow.

The invention claimed is:

1. A method of detecting cortical spreading depression (CSD) waves from EEG signals comprising:

receiving, by a computer coupled to an EEG machine, a time series of readings taken from a series of time windows from a plurality of EEG electrodes;

using a plurality of trained deep learning models executing on the computer to extract temporal features for each EEG electrode from the time series of readings from that electrode;

using a graph neural network executing on the computer, the graph neural network having trained attention layers and to aggregate the extracted temporal features to a node in the graph neural network to extract spatial information, wherein each node in the graph neural network represents a physical location of brain activity as determined from one or more of the plurality of EEG electrodes; and using a plurality of classifiers executing on the computer, the classifiers providing a binary value for each elec-

TABLE 2

| k ± SE(k) | | Trained On | | | | |
| --- | --- | --- | --- | --- | --- | --- |
| | | 20 | 32 | 64 | 128 | 256 |
| Tested | 20 | 75.73% ± 3.99 | 77.01% ± 3.80 | 76.54% ± 3.87 | 75.22% ± 4.00 | 76.31% ± 3.72 |
| On | 32 | 75.33% ± 3.21 | 77.13% ± 3.03 | 77.06% ± 3.02 | 75.88% ± 3.15 | 77.01% ± 2.94 |
| | 64 | 75.69% ± 2.25 | 77.20% ± 2.15 | 77.42% ± 2.14 | 77.28% ± 2.16 | 77.88% ± 2.09 |
| | 128 | 75.08% ± 1.54 | 76.25% ± 1.54 | 76.54% ± 1.52 | 77.13% ± 1.74 | 76.91% ± 1.54 |
| | 256 | 76.69% ± 1.10 | 78.41% ± 1.05 | 78.24% ± 1.06 | 78.63% ± 1.07 | 79.69% ± 1.02 |

As would be realized by one of skill in the art, the disclosed systems and methods described herein can be implemented by a system comprising a processor and memory, storing software that, when executed by the processor, performs the functions comprising the method. For example, the training, testing and deployment of the model can be implemented by software executing on a processor.

As would further be realized by one of skill in the art, many variations on implementations discussed herein which trode for each time window based on a probability threshold representing the presence or absence of a CSD wavefront at each respective electrode;

wherein the binary values are stitched together using a sliding time window which is assigned a temporal binary value based on a number of binary values representing the presence of CSD wavefronts present within the sliding time window; and wherein a CSD episode is determined to have occurred by temporal binary values indicating the presence of the CSD wavefronts in consecutive sliding time windows.

2. The method of claim 1 wherein each of the deep learning models is a trained convolutional neural network comprising a multi-scale 1D ResNet.

3. The method of claim 1 wherein the temporal features are extracted from a series of readings taken at midpoints from a series of time windows.

4. The method of claim 3 wherein the series of time windows comprises a series of nonoverlapping time windows.

5. The method of claim 4 wherein the series of nonoverlapping time windows comprises nonoverlapping windows of 5 minute duration.

6. The method of claim 1 wherein the graph neural network is a graph attention network.

7. The method of claim 6 wherein the graph attention network is a k-nearest neighbor graph.

8. The method of claim 7 wherein the k-nearest neighbor graph is a geometric graph that thresholds a Euclidean distance between each pair of EEG electrodes on the scalp.

9. The method of claim 1 wherein the generating step comprises inputting each node to which the temporal features have been aggregated to a respective classifier.

10. The method of claim 9 wherein each respective classifier comprises a multilayer perceptron followed by a Softmax layer.

11. The method of claim 10 wherein the Softmax layer has an output representing a spatio-temporal probability map indicating the probability distribution of a CSD wavefront for each respective EEG electrode.

12. The method of claim 1 wherein the convolutional neural network is trained using a data set having varying CSD widths, varying CSD speeds of propagation, varying numbers and placements of EEG electrodes and varying head models.

13. A system comprising:

a processor configured to execute software implementing the method of claim 1.

* * * * *